US008814932B2

(12) United States Patent
Edmunds

(10) Patent No.: US 8,814,932 B2
(45) Date of Patent: Aug. 26, 2014

(54) ANNULOPLASTY RING WITH PIERCING WIRE AND SEGMENTED WIRE LUMEN

(75) Inventor: Kevin D. Edmunds, Ham Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 200 days.

(21) Appl. No.: 13/431,407

(22) Filed: Mar. 27, 2012

(65) Prior Publication Data

US 2012/0296420 A1 Nov. 22, 2012

Related U.S. Application Data

(60) Provisional application No. 61/487,072, filed on May 17, 2011.

(51) Int. Cl.
*A61F 2/24* (2006.01)

(52) U.S. Cl.
CPC ....... *A61F 2/2445* (2013.01); *A61F 2210/0061* (2013.01); *A61F 2/2466* (2013.01); *A61F 2250/0003* (2013.01); *A61F 2250/0004* (2013.01); *A61F 2/2442* (2013.01); *A61F 2230/0091* (2013.01)
USPC .......................................... 623/2.37; 623/2.36

(58) Field of Classification Search
CPC ..................................................... A61F 2/2442
USPC ........................................................ 623/2.37
See application file for complete search history.

(56) References Cited

U.S. PATENT DOCUMENTS

| 5,064,431 | A  | 11/1991 | Gilbertson et al. |
| 5,855,565 | A  | 1/1999  | Bar-Cohen et al.  |
| 6,391,054 | B2 | 5/2002  | Carpentier et al. |
| 6,619,291 | B2 | 9/2003  | Hlavka et al.     |
| 6,676,702 | B2 | 1/2004  | Mathis            |
| 6,689,164 | B1 | 2/2004  | Seguin            |
| 6,726,716 | B2 | 4/2004  | Marquez           |
| 6,921,407 | B2 | 7/2005  | Nguyen et al.     |
| 6,997,951 | B2 | 2/2006  | Solem et al.      |
| 7,060,021 | B1 | 6/2006  | Wilk              |

(Continued)

FOREIGN PATENT DOCUMENTS

CA       2552857     *  6/2005  ................ A61F 2/06
DE  102007043831 A1     4/2009

(Continued)

OTHER PUBLICATIONS

Search Report and Written Opinion for PCT Application No. PCT/US2011/52865, mailed Jun. 13, 2012.

(Continued)

*Primary Examiner* — David Isabella
*Assistant Examiner* — Jacqueline Woznicki
(74) *Attorney, Agent, or Firm* — Vidas, Arrett & Steinkraus, P.A.

(57) ABSTRACT

An annuloplasty device having an expandable member, a plurality of lobes, and a piercing wire is herein disclosed. In some embodiments, the lobes extend radially outwardly from the expandable member. The lobes each have a wire lumen disposed therethrough, and the piercing wire is extendable through the wire lumen of each lobe to secure the device to adjacent heart tissue. In some embodiments, the expandable member comprises an inflatable medical balloon. In addition, a method of implanting an annuloplasty device is disclosed.

7 Claims, 3 Drawing Sheets

(56) References Cited

U.S. PATENT DOCUMENTS

| | | |
|---|---|---|
| 7,118,595 B2 | 10/2006 | Ryan et al. |
| 7,201,761 B2 | 4/2007 | Woolfson et al. |
| 7,296,577 B2 | 11/2007 | Lashinske et al. |
| 7,431,726 B2 | 10/2008 | Spence et al. |
| 7,635,386 B1 | 12/2009 | Gammie |
| 7,637,944 B2 | 12/2009 | Ryan et al. |
| 7,655,015 B2 | 2/2010 | Goldfarb et al. |
| 7,717,954 B2 | 5/2010 | Solem et al. |
| 2003/0078465 A1 | 4/2003 | Pai et al. |
| 2004/0133273 A1* | 7/2004 | Cox .................. 623/2.11 |
| 2004/0148021 A1 | 7/2004 | Cartledge et al. |
| 2004/0236419 A1 | 11/2004 | Milo |
| 2004/0243230 A1 | 12/2004 | Navia et al. |
| 2005/0065550 A1 | 3/2005 | Starksen et al. |
| 2005/0065601 A1 | 3/2005 | Lee et al. |
| 2005/0107812 A1 | 5/2005 | Starksen et al. |
| 2005/0137696 A1 | 6/2005 | Salahieh et al. |
| 2005/0222488 A1 | 10/2005 | Chang et al. |
| 2006/0276891 A1 | 12/2006 | Nieminen et al. |
| 2007/0027533 A1 | 2/2007 | Douk |
| 2007/0027536 A1* | 2/2007 | Mihaljevic et al. .......... 623/2.37 |
| 2007/0080188 A1 | 4/2007 | Spence et al. |
| 2007/0244556 A1 | 10/2007 | Rafiee et al. |
| 2007/0244557 A1 | 10/2007 | Rafiee et al. |
| 2008/0045977 A1 | 2/2008 | To et al. |
| 2008/0051840 A1 | 2/2008 | Moaddeb et al. |
| 2008/0065203 A1 | 3/2008 | Khalapyan |
| 2009/0177277 A1 | 7/2009 | Milo |
| 2010/0030014 A1 | 2/2010 | Ferrazzi |
| 2010/0121435 A1 | 5/2010 | Subramanian et al. |
| 2010/0280604 A1 | 11/2010 | Zipory et al. |
| 2010/0324669 A1 | 12/2010 | Hlavka et al. |
| 2011/0060407 A1* | 3/2011 | Ketai et al. .................. 623/2.37 |
| 2012/0123531 A1 | 5/2012 | Tsukashima et al. |

FOREIGN PATENT DOCUMENTS

| | | | | |
|---|---|---|---|---|
| WO | 03/075748 | | 9/2003 | |
| WO | 2005055883 A1 | | 6/2005 | |
| WO | WO 2005055883 A1 | * | 6/2005 | ............... A61F 2/06 |
| WO | 2009/135022 | | 11/2009 | |
| WO | 2010091383 A2 | | 8/2010 | |
| WO | 2010091653 A1 | | 8/2010 | |
| WO | WO 2013178335 | * | 12/2013 | ............... A61F 2/06 |

OTHER PUBLICATIONS

Search Report and Written Opinion for PCT Application No. PCT/US2012/030711, mailed Jun. 13, 2012.

Search Report and Written Opinion for PCT Application No. PCT/US2011/52976, mailed Jun. 1, 2012.

U.S. Appl. No. 61/487,083 entitled "Annuloplasty Ring with Anchors Fixed by Curing Polymer," and filed May 17, 2011.

U.S. Appl. No. 61/487,065, entitled "Percutaneous Mitral Annulus Mini-Plication," and filed May 17, 2011.

U.S. Appl. No. 61/487,053, entitled "Positioning Cage," and filed May 17, 2011.

U.S. Appl. No. 61/487,063, entitled "Corkscrew Annuloplasty Device," and filed May 17, 2011.

\* cited by examiner

ANNULOPLASTY RING WITH PIERCING WIRE AND SEGMENTED WIRE LUMEN

CROSS-REFERENCE TO RELATED APPLICATIONS

This application claims priority to U.S. provisional application Ser. No. 61/487,072, filed May 17, 2011, the contents of which are hereby incorporated by reference.

STATEMENT REGARDING FEDERALLY SPONSORED RESEARCH

Not Applicable.

FIELD OF THE INVENTION

The invention relates to an annuloplasty ring for repairing heart valves, and, in some embodiments, mitral valves.

BACKGROUND OF THE INVENTION

In an effort to stem the risk of heart valve disease, various medical procedures have been developed to repair or replace poorly functioning or stenosed heart valves. In particular, annuloplasty procedures have been used to repair heart valves by way of open heart surgery or, on a more limited basis, by way of less invasive techniques.

Mitral regurgitation is a particular type of heart valve disease wherein the mitral valve fails to sufficiently close, and blood is allowed to backflow across the valve. Consequently, many mitral annuloplasty procedures are designed to make the mitral annulus smaller, particularly in the septal—lateral dimension, allowing the mitral valve leaflets to coapt more effectively and preventing mitral regurgitation.

In some instances, repair of the mitral valve involves placing an annuloplasty ring on the mitral valve. Certain procedures involve suture-based cinching to reshape the mitral valve. In addition, some percutaneous annuloplasty procedures involve placing a rigid structure in the coronary sinus, which is near but not exactly at, the actual location of the mitral annulus. Such procedures can be cumbersome and may not be particularly effective or safe in all patients due to the anatomy of the coronary sinus, the mitral annulus, and the nearby circumflex coronary artery. In particular, coronary sinus devices may not be as effective as surgically placed devices, and crossing of the coronary sinus over the circumflex artery can cause dangerous compression of the artery by an annular cinching device placed in the coronary sinus.

Heretofore, reliable anchoring of an annuloplasty ring at a desirable location has been difficult using percutaneous and less invasive techniques. In addition, some prior attempts have utilized rather stiff structures in order to obtain the required shape and support for the valve. Consequently, there is a need for an annuloplasty procedure and device that overcomes the problems associated with prior approaches and devices.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In some embodiments, and as discussed in more detail below, an annuloplasty device comprises an expandable member, a plurality of lobes extending from the expandable member, and a piercing wire. In some embodiments, the lobes extend radially outwardly from the expandable member, and each lobe has a wire lumen disposed through the lobe. The piercing wire is extendable through the wire lumens.

In some embodiments, a method of implanting an annuloplasty device comprises providing an annuloplasty device, the annuloplasty device comprising an expandable medical balloon, a plurality of lobes extending radially from the expandable medical balloon, and a piercing wire. Each of the lobes has a wire lumen extending therethrough. In some embodiments, the method of implanting an annuloplasty device further comprises inserting the annuloplasty device adjacent the mitral annulus, expanding the expandable medical balloon, and inserting the piercing wire through portions of the mitral annulus and through the wire lumens of the lobes.

BRIEF DESCRIPTION OF THE SEVERAL VIEWS OF THE DRAWING(S)

DETAILED DESCRIPTION OF THE INVENTION

Figure 1:
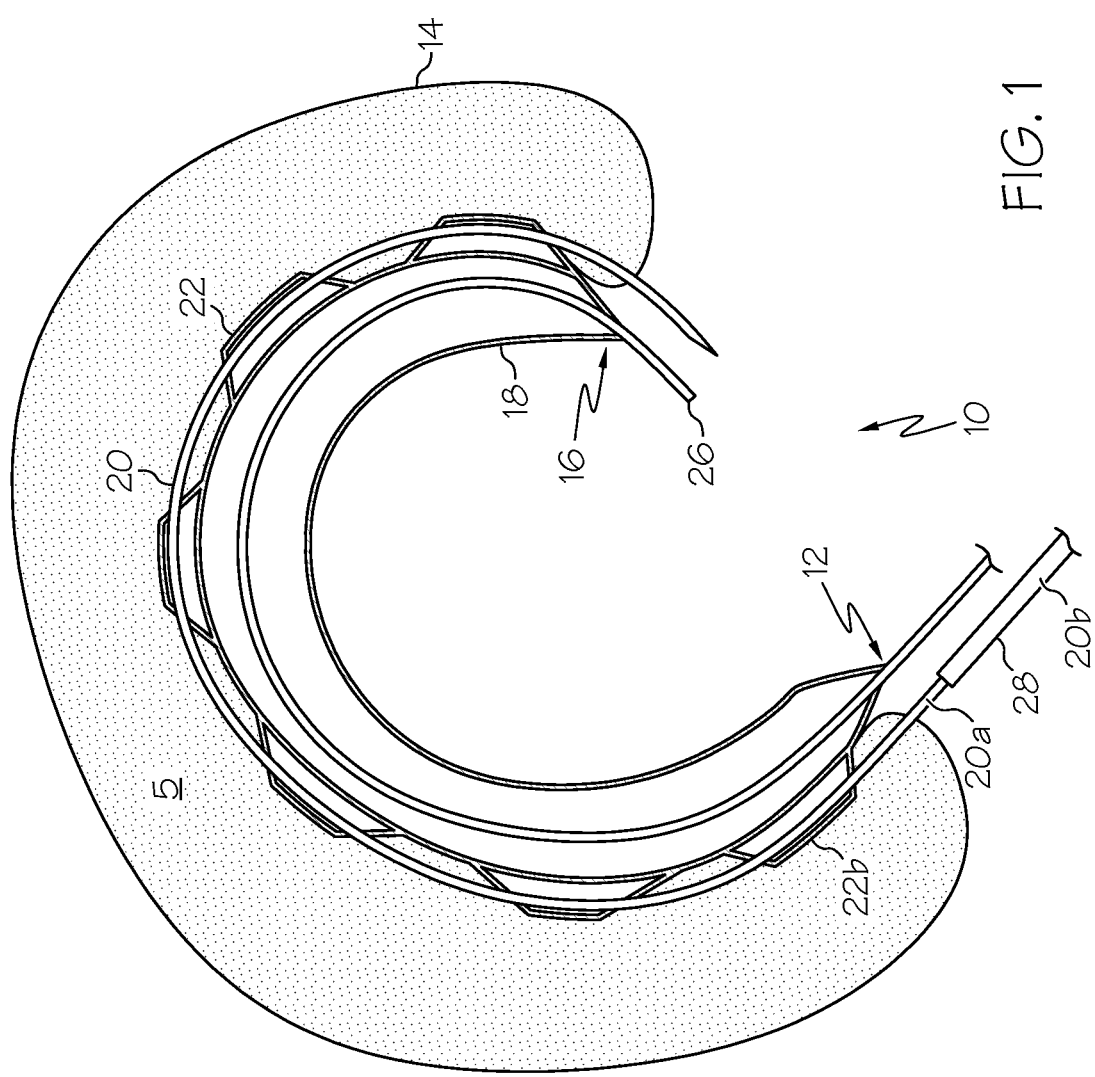
FIG. 1 shows a top view of the mitral annulus having an annuloplasty device attached thereto.
Figure 2:
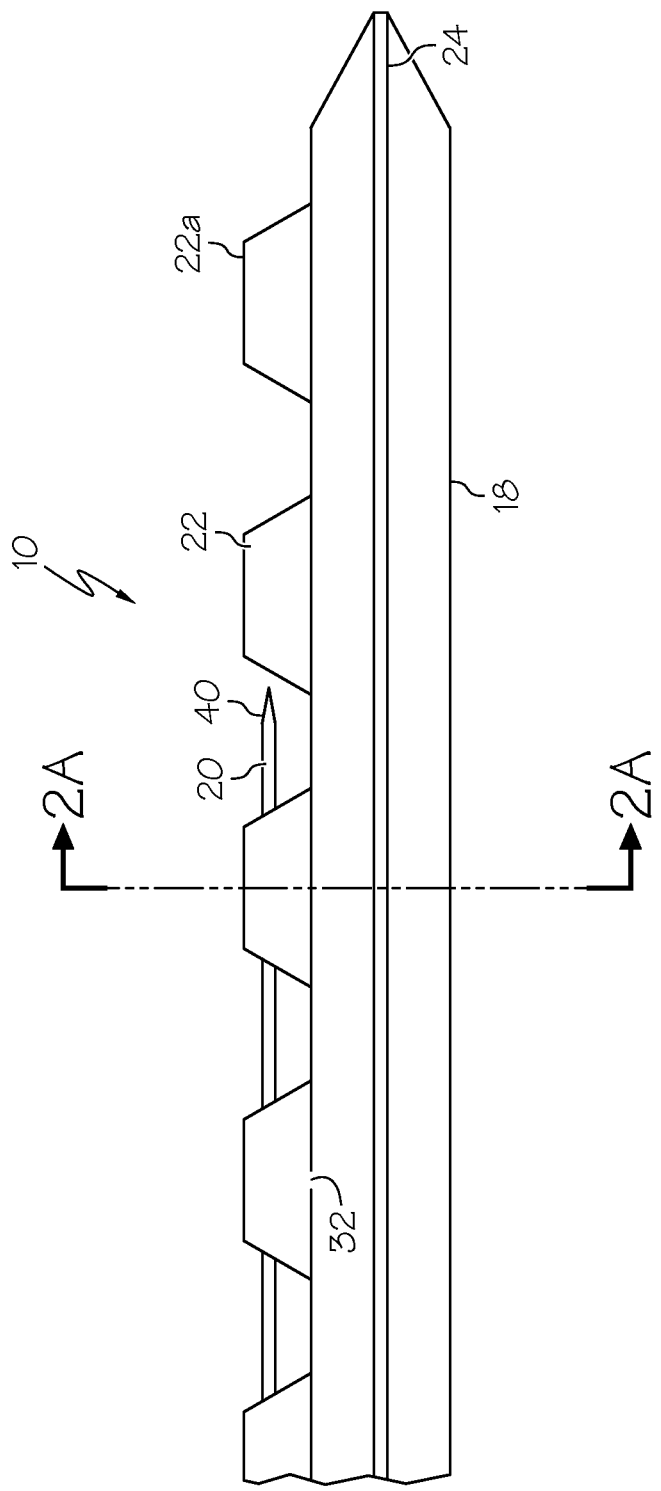
FIG. 2 shows a partial cut-away side view of an annuloplasty device.
Figure 2A:
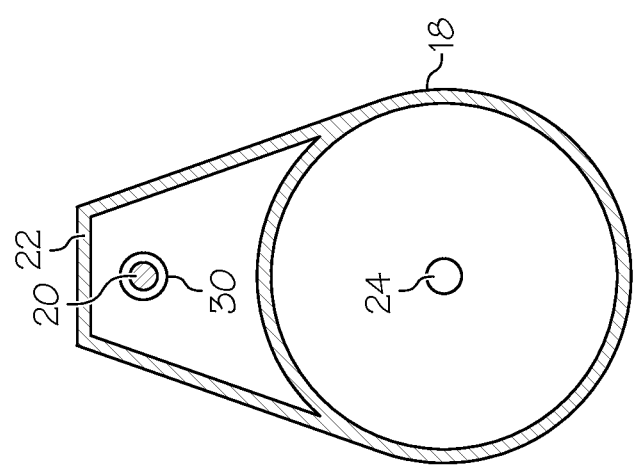
FIG. 2A shows a cross-sectional view of the annuloplasty device of FIG. 2.

In at least one embodiment, an annuloplasty device 10 comprises an expanding member 18 and a piercing wire 20. The annuloplasty device 10 further comprises a plurality of lobes 22 extending radially from the expanding member 18. In some embodiments, the lobes 22 are attached to the expanding member 18. And, in some embodiments, the lobes 22 expand in conjunction with the expanding member 18 and are forced outwardly into adjacent heart tissue 5, for example of the mitral annulus 14.

The expanding member 18 comprises a proximal end 12 and a distal end 16. In some embodiments, the expanding member 18 further comprises a guidewire lumen 24 through which a guidewire 26 is disposed. In some embodiments, the expanding member 18 comprises an expandable balloon. Alternatively, in some embodiments, the expanding member 18 comprises a mesh expander, for example as disclosed in U.S. Pat. No. 5,449,372 to Schmaltz et al., which is herein incorporated by reference. In some embodiments, the mesh expander comprises a wire braid with actuating elements attached at either end of the wire braid. The actuating elements are moved axially apart from one another or closer together to radially contract or expand the wire braid. In this regard, in some embodiments, such a mesh expander is used to press the expandable lobes 22 against the adjacent heart tissue 5, thereby permitting the piercing wire 20 to pass through the tissue 5.

In some embodiments, the mesh expander is coated with a plastic coating that forces the lobes 22 into the adjacent tissue 5. Further, in some embodiments, the mesh expander has a plurality of eyelets attached thereto. The eyelets serve as lobes 22, allowing for the piercing wire 20 to be threaded therethrough.

In addition, in some embodiments, the annuloplasty device 10 is pressed against the adjacent heart tissue 5 by way of a coil body expander, for example as disclosed in U.S. Pat. No. 5,441,516 to Wang et al., or as disclosed in U.S. Pat. No. 5,855,565 to Bar-Cohen et al., which are incorporated by reference. In some embodiments, the annuloplasty device 10 includes a curved or actuated stylet to bias the expanding member 18 larger or smaller. Any other suitable mechanisms or methods can also be used.

In some embodiments, the lobes 22 are attached to an outer surface of the expanding member 18. In some embodiments, for example where the expanding member 18 comprises an expandable balloon, one or more of the lobes 22 shares an inflation lumen with the expandable balloon such that the lobes and the expandable balloon are expanded concurrently. Moreover, in some embodiments, for example where the expanding member 18 comprises an expandable balloon, the expandable balloon comprises one or more ports 32 through which fluid can flow to expand one or more of the lobes 22, as desired.

In some embodiments, the lobes 22 are attached to the expanding member 18 with an adhesive. In some embodiments, the lobes 22 are attached to the expanding member 18 by way of thermal or chemical bonding, or by tie elements such as rings disposed over a portion of the lobes 22. In some embodiments, however, the lobes 22 and the expanding member 18 are formed from a single extrusion, and portions of the extrusion are removed to create the lobes 22.

Turning now to the piercing wire 20, the piercing wire 20 is inserted into the heart tissue 5 after the expanding member 18 is expanded and the lobes 22 press up against portions of the heart tissue 5. More particularly, in some embodiments, expansion of the expanding member 18 and the lobes 22 forces the heart tissue 5 to deform, with heart tissue 5 protruding between longitudinally adjacent lobes 22. After the expanding member 18 and lobes 22 are positioned, the piercing wire 20 is inserted through the piercing wire lumen 30 and through the heart tissue 5 between longitudinally adjacent lobes 22. In this regard, the piercing wire 20 passes through each lobe 22 and through the adjacent heart tissue 5, to produce an interrupted attachment of the annuloplasty device 10 to the heart tissue 5. In combination, the piercing wire lumens 30 of the lobes 22 form a segmented wire lumen.

In order to ensure that the piercing wire 20 lines up with the wire lumens 30 of each lobe 22 as the piercing wire 20 is being inserted, the lobes 22 are comprised of a rigid or semi-rigid material. Consequently, the lobes 22 deform heart tissue 5 so that the piercing wire 20 tracks into the next wire lumen 30.

After the piercing wire 20 is inserted, in some embodiments, it can be used to cinch the annuloplasty device 10 into a smaller dimension. In particular, in some embodiments, after the piercing wire 20 extends through the lobes 22, the distal end 40 of the piercing wire 20 is anchored or secured to the distal most lobe 22a. In some embodiments, the piercing wire 20 is secured to the distal most lobe 22a for example by way of a ratcheting mechanism, linear or cylindrical taper wedge, spring-loaded latch, or deformable end on the piercing wire or distal most lobe 22a which plastically deforms as the piercing wire 20 is inserted into the distal most lobe 22a. In some embodiments, the piercing wire 20 is secured to the distal most lobe 22a, for example, by thermal or chemical bonding. In some embodiments, the annuloplasty device 10 facilitates cinching of the annulus 14 between each lobe 22.

In some embodiments, the distal most lobe 22a has at least one tooth which operably fits into a sear, catch, or barb located within a portion of the distal most lobe 22a. Thus, once the piercing wire 20 is inserted into the distal most lobe 22a, in some embodiments, it is held from moving proximally out of the distal most lobe 22a. In addition, once the distal end 40 of the piercing wire 20 is secured to the distal most lobe 22a, a proximal portion of the piercing wire 20 is pulled (from outside the patient's body) to cinch the annuloplasty device 10 into a smaller dimension. Subsequently, after cinching the annuloplasty device 10, in some embodiments, a proximal portion of the piercing wire 20 is secured to the proximal most lobe 22b (FIG. 1), for example by way of a ratcheting mechanism, linear or cylindrical taper wedge, spring-loaded latch, or deformable section on the piercing wire 20 or proximal most lobe 22b which plastically deforms. In some embodiments, the piercing wire 20 is secured to the proximal most lobe 22b, for example, by thermal or chemical bonding. Other methods of securement can also be used, for example as disclosed in the Application titled "Corkscrew Annuloplasty Device," provisionally filed on May 17, 2011, and filed as a non-provisional application on Sep. 23, 2011, with application Ser. No. 13/241,603, which is incorporated by reference. The Application titled "Corkscrew Annuloplasty Device" subsequently published as Publication No. 2012/0296417. In addition, and to the extent possible, other features disclosed in the "Corkscrew Annuloplasty Device" application can be incorporated into the annuloplasty device 10 of the immediate application.

In addition to the foregoing, in some embodiments, the proximal end of the piercing wire 20 extends outside the patient's body, for example to a catheter hub, so the piercing wire can be manipulated during surgery. In some embodiments, the piercing wire 20 comprises a single wire which is severed near the proximal end 12 of the expanding member 18. The piercing wire 20 can be severed by shearing, slicing, scoring, electrolytic separation, melting, or in any other suitable manner. Alternatively, in some embodiments, the piercing wire 20 comprises two segments 20a, 20b coupled together at a coupler 28. In some embodiments, the two segments 20a, 20b are connected with a threaded connection, for example, by threading segment 20a into segment 20b. Alternatively, in some embodiments, the segments 20a, 20b are connected with a separable latch, ring, or pin, for example as disclosed in "Corkscrew Annuloplasty Device," Publication No. 2012/0296417. Also as disclosed in the "Corkscrew Annuloplasty Device," in some embodiments, the immediate annuloplasty device 10 comprises a looping wire that extends between distal end of the piercing wire (or core wire, if present) to the proximal end 12 of the annuloplasty device 10 in order to secure or cinch the device 10 into a reduced dimension.

In some embodiments, the annuloplasty device 10 further comprises a stiffening member, for example as disclosed in the Application entitled "Annuloplasty Ring with Anchors Fixed by Curing Polymer", provisionally filed May 17, 2011, and filed as a non-provisional application on Sep. 23, 2011, with Application Ser. No. 13/242,953, which is hereby incorporated by reference. The Application entitled "Annuloplasty Ring with Anchors Fixed by Curing Polymer" subsequently published as Publication No. 2012/0296419. In particular, in some embodiments, the stiffening member biases the annuloplasty device 10 in a cinched or reduced configuration, for example in the septal-lateral dimension. Alternatively, in some embodiments, the stiffening member is positioned in the annuloplasty device 10 to maintain the device 10 in a generally straight configuration during insertion; then, the stiffening member is removed, allowing the annuloplasty device 10 to take on a curved, semi-circular, or other desired configuration for attachment to adjacent heart tissue 5. In some embodiments, the piercing wire 20 functions as a stiffening member.

In some embodiments, the annuloplasty device 10 further comprises an inflation and deflation lumen, through which fluid is injected and/or removed to permit inflation and/or deflation of the annuloplasty device 10 and/or lobes 22.

The annuloplasty device 10 comprises any suitable materials. For example, in some embodiments, the piercing wire comprises a metallic material such as stainless steel, Nitinol, or any other suitable alloy. In addition, in some embodiments, the expanding member 18 and the lobes 22 comprise a polymeric material.

Although particular features are shown or described with respect to particular embodiments disclosed herein, it will be appreciated that these features can be combined with the features or substituted for the features of other embodiments.

In addition, the Applications entitled "Percutaneous Mitral Annulus Mini-Plication," with Publication No. 2012/0296349, and "Positioning Cage," with Publication No. 2012/0296160, are hereby incorporated by reference. In particular, certain features shown and described in these applications (and those incorporated by reference elsewhere) can be incorporated into the annuloplasty device of the immediate application. Moreover, in some embodiments, the Positioning Cage of the application by the same name is used to perform implantation of the annuloplasty device of the immediate application.

In some embodiments, the annuloplasty device 10 is inserted from a retrograde arterial access or trans-septal access. In some embodiments, for example where the annuloplasty device 10 is positioned for intracardiac deployment, the annuloplasty device 10 is used in combination with the guidewire 26. In some embodiments, the guidewire 26 is inserted via a femoral vein access. After the guidewire 26 is in place, in some embodiments, the annuloplasty device 10 is inserted over the guidewire 26, crossing the atrial septum, to reach the atrial side of the mitral annulus 14. After this, the annuloplasty device 10 is positioned at the mitral annulus 14.

In some embodiments, the annuloplasty device 10 is secured to the epicardial surface of the heart. In some embodiments, the annuloplasty device 10 is inserted via a pericardial access, minimally invasive transthoracic approach, to access an external portion of the heart in the region of the mitral annulus. When this method is employed, however, care must be taken to avoid damage to the major epicardial blood vessels during implantation, anchoring, and cinching of the annuloplasty device 10.

In some embodiments, the annuloplasty device 10 is used on a tricuspid valve, for performing tricuspid valve annuloplasty.

The above disclosure is intended to be illustrative and not exhaustive. This description will suggest many variations and alternatives to one of ordinary skill in this field of art. All these alternatives and variations are intended to be included within the scope of the claims where the term "comprising" means "including, but not limited to." Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

What is claimed is:

1. An annuloplasty device comprising:
   an expandable member comprising an expandable balloon, the expandable balloon including a plurality of ports;
   a plurality of lobes extending radially from the expandable member, each lobe having a wire lumen disposed therethrough; and
   a piercing wire, the piercing wire extendable through the wire lumen of each lobe;
   wherein each port extends between the expandable balloon and one of the lobes.

2. The annuloplasty device of claim 1, wherein the expandable member defines a guidewire lumen extending through the expandable member.

3. The annuloplasty device of claim 1, wherein the piercing wire is biased in a semi-circular shape.

4. The annuloplasty device of claim 1, wherein the lobes are attached to the expandable member with an adhesive.

5. The annuloplasty device of claim 1, wherein the piercing wire comprises two segments, the two segments coupled together via a coupler.

6. The annuloplasty device of claim 1, wherein the plurality of lobes includes a distal most lobe and a proximal most lobe, a portion of the piercing wire being secured to the distal most lobe upon insertion of the piercing wire into the distal most lobe.

7. The annuloplasty device of claim 6, wherein a portion of the piercing wire is secured to the proximal most lobe upon insertion of the piercing wire into the proximal most lobe.

* * * * *